(12) United States Patent
Stout

(10) Patent No.: US 8,361,020 B2
(45) Date of Patent: Jan. 29, 2013

(54) CATHETER ASSEMBLY AND PIERCED SEPTUM VALVE

(75) Inventor: Marty L. Stout, South Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/042,073

(22) Filed: Mar. 7, 2011

(65) Prior Publication Data

US 2012/0016301 A1 Jan. 19, 2012

Related U.S. Application Data

(60) Provisional application No. 61/364,576, filed on Jul. 15, 2010.

(51) Int. Cl.
*A61M 5/36* (2006.01)

(52) U.S. Cl. .............. 604/122; 604/167.01; 604/236; 604/533; 604/537

(58) Field of Classification Search ............. 604/523, 604/533–535, 537, 539, 236, 167.01–167.04, 604/167.06, 256, 264, 122
See application file for complete search history.

(56) References Cited

U.S. PATENT DOCUMENTS

| | | | |
|---|---|---|---|
| 4,387,879 A | 6/1983 | Tauschinski | |
| 4,449,693 A | 5/1984 | Gereg | |
| 4,758,225 A | 7/1988 | Cox et al. | |
| 4,842,591 A | 6/1989 | Luther | |
| 4,874,377 A | 10/1989 | Newgard et al. | |
| 4,917,668 A | 4/1990 | Haindl | |
| 4,935,010 A | 6/1990 | Cox et al. | |
| 4,950,257 A | 8/1990 | Hibbs et al. | |
| 5,041,097 A | 8/1991 | Johnson | |
| 5,053,014 A | 10/1991 | Van Heugten | |
| 5,062,836 A | 11/1991 | Wendell | |
| 5,064,416 A | 11/1991 | Newgard et al. | |
| 5,084,023 A | 1/1992 | Lemieux | |
| 5,085,645 A | 2/1992 | Purdy et al. | |
| 5,108,374 A | 4/1992 | Lemieux | |
| 5,127,905 A | 7/1992 | Lemieux | |
| 5,154,703 A | 10/1992 | Bonaldo | |
| 5,156,596 A | 10/1992 | Balbierz et al. | |
| 5,234,410 A | 8/1993 | Graham et al. | |
| 5,290,246 A * | 3/1994 | Yamamoto et al. ...... | 604/167.03 |
| 5,295,969 A | 3/1994 | Fischell et al. | |
| 5,330,435 A | 7/1994 | Vaillancourt | |
| 5,350,363 A | 9/1994 | Goode et al. | |
| 5,352,205 A | 10/1994 | Dales et al. | |
| 5,405,323 A | 4/1995 | Rogers et al. | |
| 5,456,675 A | 10/1995 | Wolbring et al. | |
| 5,487,728 A | 1/1996 | Vaillancourt | |

(Continued)

FOREIGN PATENT DOCUMENTS

CA 2133053 A1 3/1995
DE 20 2009 009 602 U1 1/2010

(Continued)

*Primary Examiner* — Quynh-Nhu H Vu
(74) *Attorney, Agent, or Firm* — Jeanne Lukasavage; Craig Metcalf; Kirton McConkie

(57) ABSTRACT

A pierced septum valve is disclosed herein. The pierced septum valve includes a septum that is located within a lumen of a body. A septum activator is positioned proximal the septum within the lumen of the body. A seal is disposed between an outer surface of the septum activator and the body to seal the portion of the septum activator distal the lumen from the portion of the septum activator proximal the lumen. One or more vents are disposed between the seal and the lumen of the body to permits the passage of air but not blood past the seal.

20 Claims, 9 Drawing Sheets

U.S. PATENT DOCUMENTS

| | | | |
|---|---|---|---|
| 5,520,666 A | 5/1996 | Choudhury et al. | |
| 5,549,566 A | 8/1996 | Elias et al. | |
| 5,549,577 A | 8/1996 | Siegel et al. | |
| 5,575,769 A | 11/1996 | Vaillancourt | |
| 5,613,663 A | 3/1997 | Schmidt et al. | |
| 5,651,772 A | 7/1997 | Arnett | |
| 5,657,963 A | 8/1997 | Hinchliffe et al. | |
| 5,697,915 A | 12/1997 | Lynn | |
| 5,738,144 A | 4/1998 | Rogers | |
| 5,749,861 A * | 5/1998 | Guala et al. | 251/149.1 |
| 5,806,831 A | 9/1998 | Paradis | |
| 5,817,069 A | 10/1998 | Arnett | |
| 5,911,710 A | 6/1999 | Barry et al. | |
| 5,954,698 A | 9/1999 | Pike | |
| 5,967,490 A | 10/1999 | Pike | |
| 6,039,302 A | 3/2000 | Cote, Sr. et al. | |
| 6,077,244 A | 6/2000 | Botich et al. | |
| 6,117,108 A | 9/2000 | Woehr et al. | |
| 6,171,287 B1 | 1/2001 | Lynn et al. | |
| 6,273,869 B1 | 8/2001 | Vaillancourt | |
| 6,485,473 B1 | 11/2002 | Lynn | |
| 6,575,960 B2 | 6/2003 | Becker et al. | |
| 6,595,981 B2 * | 7/2003 | Huet | 604/523 |
| 6,699,221 B2 | 3/2004 | Vaillancourt | |
| 6,719,726 B2 | 4/2004 | Meng et al. | |
| 6,740,063 B2 | 5/2004 | Lynn | |
| 6,883,778 B1 | 4/2005 | Newton et al. | |
| 7,008,404 B2 | 3/2006 | Nakajima | |
| 7,347,839 B2 | 3/2008 | Hiejima | |
| 7,396,346 B2 | 7/2008 | Nakajima | |
| 7,470,254 B2 | 12/2008 | Basta et al. | |
| 7,736,339 B2 * | 6/2010 | Woehr et al. | 604/164.08 |
| 7,914,494 B2 | 3/2011 | Hiejima | |
| 2006/0163515 A1 | 7/2006 | Ruschke | |
| 2007/0083157 A1 | 4/2007 | Belley et al. | |
| 2007/0083162 A1 | 4/2007 | O'Reagan et al. | |
| 2007/0233007 A1 | 10/2007 | Adams | |
| 2008/0039796 A1 | 2/2008 | Nakajima | |
| 2008/0108944 A1 | 5/2008 | Woehr et al. | |
| 2010/0204675 A1 | 8/2010 | Woehr et al. | |
| 2010/0222746 A1 | 9/2010 | Burkholz | |
| 2011/0130728 A1 | 6/2011 | McKinnon | |

FOREIGN PATENT DOCUMENTS

| | | |
|---|---|---|
| EP | 1 679 043 A1 | 7/2006 |
| WO | 99/34849 | 7/1999 |
| WO | WO 99/34849 | 7/1999 |
| WO | 2008/052790 A2 | 5/2008 |
| WO | 2010/093791 A1 | 8/2010 |

* cited by examiner

CATHETER ASSEMBLY AND PIERCED SEPTUM VALVE

This application claims the benefit of U.S. Provisional Application No. 61/364,576 filed Jul. 15, 2010, entitled PIERCED SEPTUM BLOOD CONTROL VALVE WITH A FLOW RESTRICTOR AND A BLOOD VALVE FORMING A TERTIARY FLASHBACK CHAMBER. This application claims priority to and incorporates by reference the provisional application.

BACKGROUND

Catheters are commonly used for a variety of infusion therapies. For example, catheters are used for infusing fluids, such as normal saline solution, various medicaments, and total parenteral nutrition into a patient; withdrawing blood from a patient; or monitoring various parameters of the patient's vascular system. Catheters are typically coupled to a catheter adapter that supports catheter and provides for an attachment to IV tubing. Generally, following placement of the catheter into the vasculature of a patient, the catheter adapter may be coupled to a fluid source via a section of IV tubing to infuse fluids into the patient.

In order to verify proper placement of the catheter in the blood vessel, the clinician generally confirms that there is "flashback" of blood from the patient's vasculature into a flashback chamber of the catheter or catheter adapter. Once proper placement of the catheter is confirmed, the clinician must attach the catheter adapter to a section of IV tubing, or continue to manually occlude the vein to prevent undesirable exposure to blood. The process of coupling the catheter adapter to the section of IV tubing requires the clinician to awkwardly maintain pressure on the vein of the patient while simultaneously coupling the catheter adapter and the IV tubing. A common, yet undesirable practice is to permit blood to temporarily and freely flow from the catheter adapter while the clinician locates and couples the IV tubing to the catheter adapter. Another common practice is to attach the catheter adapter to the IV tubing prior to placing the catheter into the vein of the patient. While this method may prevent undesirable exposure to blood, positive pressure from the IV tubing into the catheter can does not permit desirable flashback and thus reduces a clinician's ability to confirm proper catheter placement.

Accordingly, there is a need in the art for a catheter assembly that permits controlled, desirable flashback without the risk of encountering undesirable exposure to blood. Such a catheter assembly is disclosed herein.

SUMMARY

In order to overcome the limitations discussed above, the present invention relates to a pierced septum valve that provides selective activation of fluid flow through the catheter assembly while minimizing or eliminating blood exposure. Furthermore, confirmation of catheter placement can be enhanced with an additional flash chamber that is created by including a seal around the exterior of the septum activator. The combination of the pierced septum valve and the seal about the septum activator can provide a longer flashback period in which clinicians can assure that a catheter is properly placed in a blood vessel of a patient.

In one aspect, a pierced septum valve includes a septum, a septum activator, a seal and one or more vents. The septum is disposed within a lumen of a body. A septum activator is disposed proximal the septum within the lumen of the body. A seal is disposed between an outer surface of the septum activator and the body. The seal seals the portion of the septum activator distal the seal from the portion of the septum activator proximal the seal. One or more vents are disposed between the seal and the lumen of the body, the one or more vents each having a cross sectional area that permits the passage of air but not blood.

Some implementations include one or more of the following aspects. The cross sectional area of each vent can be between 0.0001 to 0.0003 inches$^2$. The one or more vents can include six or more vents. The seal can encircle the septum activator. The one or more vents can be formed in the exterior of the seal. The one or more vents can be formed through the seal. The one or more vents can be channels formed in the body. The body can be a catheter adapter and the lumen of the body can extend through the catheter adapter. The seal can have an outer diameter greater than or equal to an inner diameter of the lumen. The seal can include an elastomeric material. The seal can be disposed about a proximal portion of the septum activator.

In another aspect, a catheter assembly includes a catheter adapter, a septum, and a septum activator, a seal, one or more flow restrictors, and one or more vents. The catheter adapter has a lumen extending therethrough. The septum is disposed within the lumen. One or more flow restrictors are disposed between the septum and the catheter adapter. A septum activator is disposed within the lumen proximal the septum. A seal is disposed between an outer surface of the septum activator and the catheter adapter. The seal seals the portion of the septum activator distal the seal from the portion of the septum activator proximal the seal. One or more vents are disposed in the seal.

Some implementations include one or more of the following aspects. The one or more vents disposed in the seal can each have a cross sectional area between 0.0001 to 0.0003 inches$^2$. The one or more flow restrictors include one or more openings each having a cross sectional area of greater than 0.0003 inches$^2$. The volume exterior the septum activator between the septum and the seal can form a flashback chamber. The septum activator can have a substantially tubular-shaped body with a lumen extending therethrough. The seal can have an outer diameter greater than or equal to an inner diameter of the lumen at the locations. The seal can be disposed about a proximal portion of the septum activator. The seal can include an elastomeric material.

In another aspect, a catheter assembly includes a catheter adapter, a septum, a septum activator, an annular seal, and one or more vents. The catheter adapter has a lumen extending therethrough. The septum is disposed within the lumen. One or more flow restrictor channels are disposed between the septum and the catheter adapter. The cross sectional area of each of the flow restrictor channels is greater than 0.0003 inches$^2$. The septum activator is disposed within the lumen proximal the septum, the septum activator has a substantially tubular-shaped body. An annular seal is disposed between an outer surface of the septum activator and an inner surface of the lumen. The seal encircles a proximal portion of the septum activator. One or more vents are disposed between the seal and the lumen of the body. The one or more vents each have a cross sectional area between 0.0001 to 0.0003 inches$^2$.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

Embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
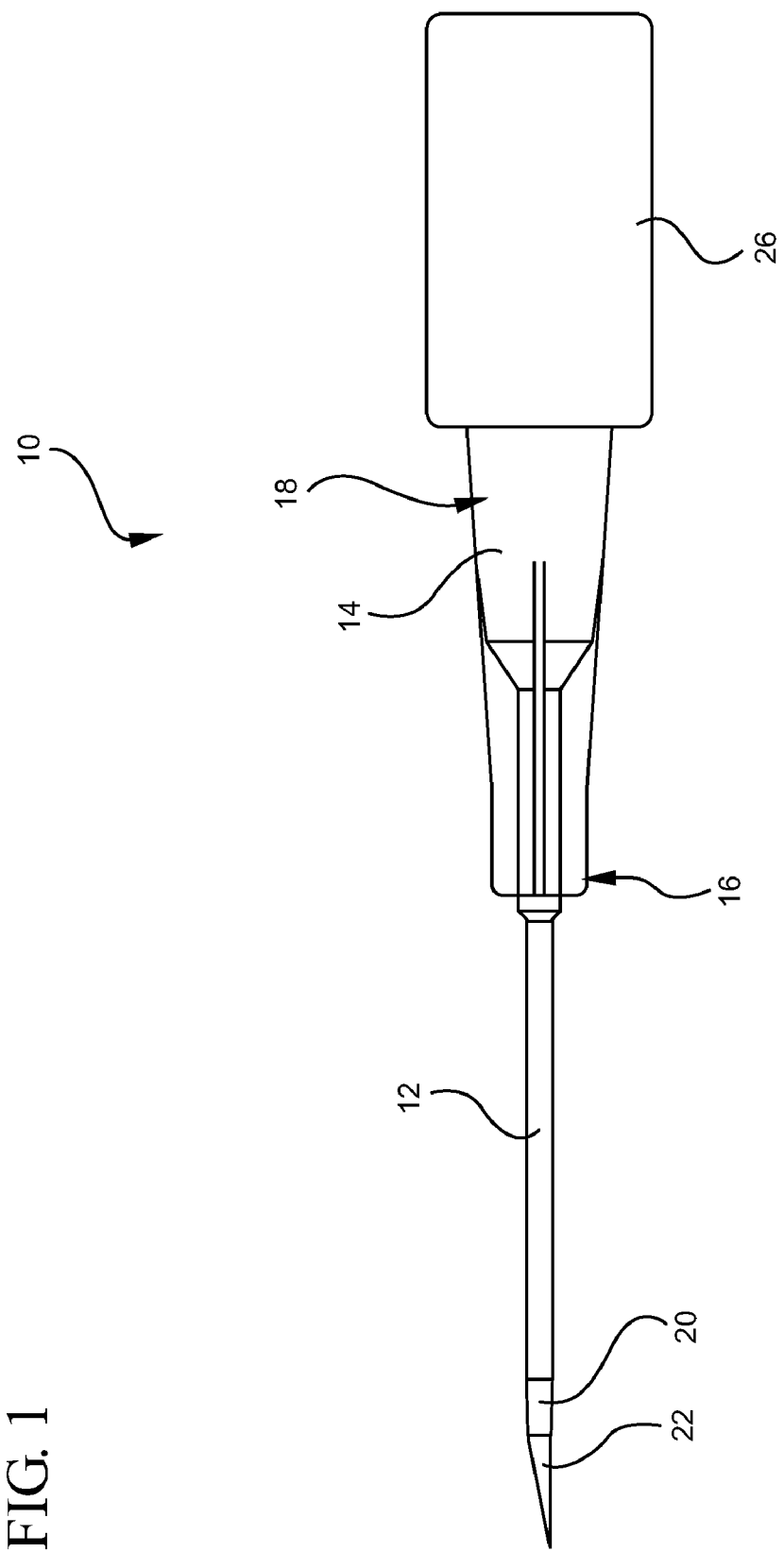
FIG. 1 is a perspective view of a catheter assembly, according to some embodiments.

Referring now to FIG. 1, a catheter assembly 10 is illustrated. The catheter assembly 10 generally includes a catheter 12 coupled to a distal end 16 of a catheter adapter 14. The catheter 12 and the catheter adapter 14 are integrally coupled such that an inner lumen of the catheter adapter 14 is in fluid communication with an inner lumen of the catheter 12. The catheter 12 generally comprises a biocompatible material having sufficient rigidity to withstand pressures associated with insertion of the catheter into a patient.

In some embodiments, as shown, the catheter 12 is an over-the-needle catheter that is made of a flexible or semi-flexible polymer material and which may be used in combination with a rigid introducer needle 22. The rigid introducer needle 22 enables the insertion of the non-rigid over-the-needle catheter into a patient. The introducer needle 22 can be coupled to a needle hub 26 that is selectively coupled to the proximal end 18 of the catheter adapter 14. The introducer needle 22 is typically inserted through the catheter 12 such that a tip of the needle 22 extends beyond the tapered tip 20 of the catheter 12. Insertion of the introducer needle 22 into the vein of the patient creates an opening in the vein through which the tapered tip 20 of the catheter 12 is inserted. The outer surface of the tapered tip 20 enables gradual insertion of the catheter 12 into the opening.

In other embodiments, the catheter 12 is not an over-the-needle catheter, but comprises a rigid, polymer material, such as vinyl. Rigid catheters can include a beveled cutting surface that is utilized to provide an opening in a patient to permit insertion of the catheter 12 into the vascular system of the patient. Accordingly, in some embodiments, the catheter 12 comprises a metallic material, such as titanium, stainless steel, nickel, molybdenum, surgical steel, and alloys thereof. Still, in other embodiments, surgically implanted catheters may also be used in combination with the present invention.

The catheter 12 can be a peripheral-type intravenous catheter that generally comprises a short or truncated catheter for insertion into a small peripheral vein. Such catheters generally comprise a diameter of about a 14-gauge catheter or smaller (on a Stubs scale), and is between about 13 mm to 52 mm in length. Peripheral intravenous catheters are typically designed for temporary placement. The short length of the catheter facilitates convenient placement of the catheter. In other embodiments, the catheter 12 is a midline or central catheter, which may be longer and used for more extended periods.

Figure 2:
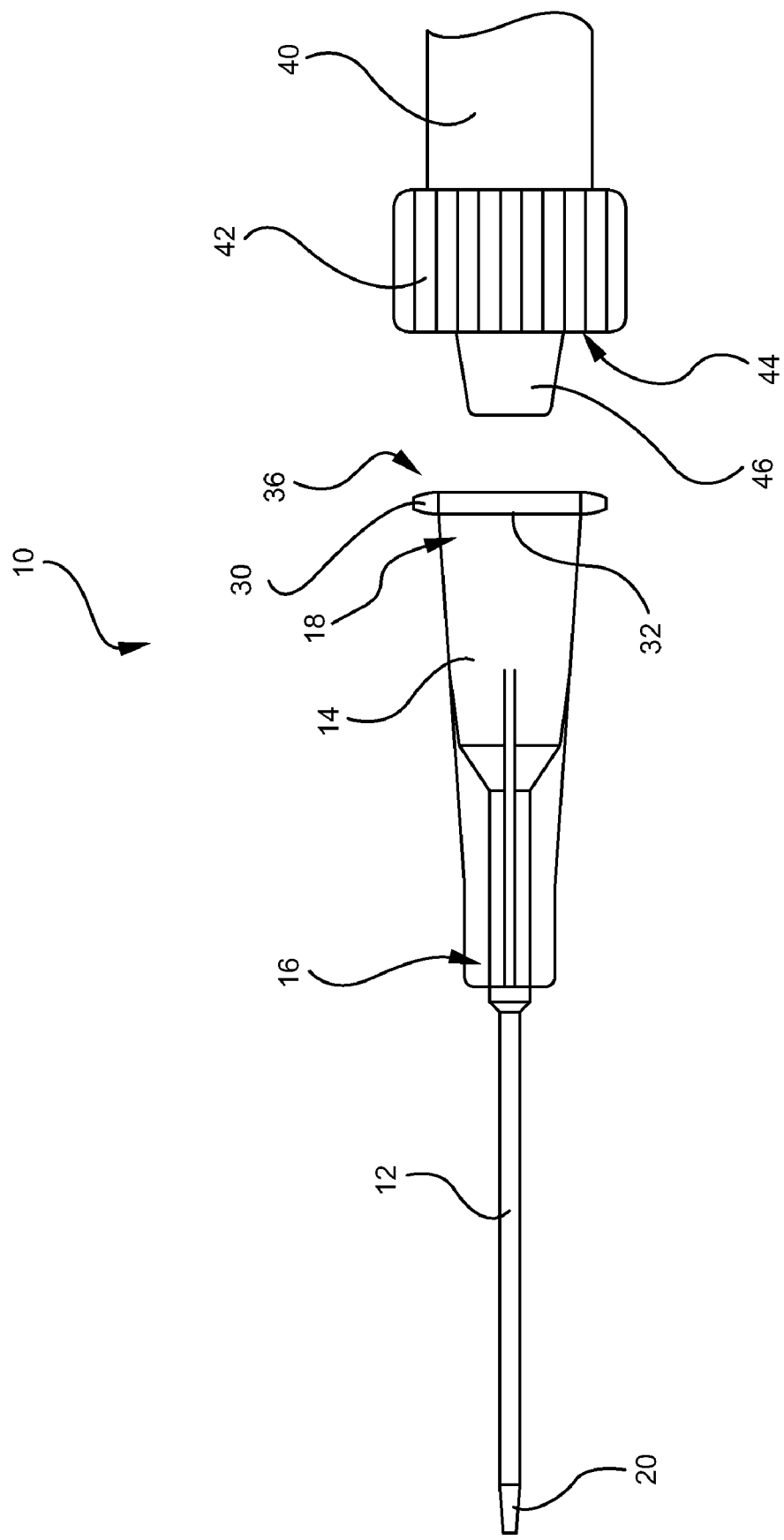
FIG. 2 is a perspective view of a catheter assembly following removal of an introducer needle, according to some embodiments.

Referring now to FIG. 2, once the catheter 12 is inserted into the vein of the patient, the introducer needle 22 is removed proximally from the catheter 12 to provide a fluid conduit through the interior lumen 36 of the catheter 12, which can be connected to a fluid source. In some embodiments, a portion of the catheter 12 and/or catheter adapter 14 can be connected to a section of intravenous tubing 40 to further facilitate delivery of a fluid to or removal of a fluid from a patient. In some embodiments, a proximal end 18 of the catheter adapter 14 includes a flange 32. The flange 32 provides a positive surface that may be configured to enable coupling of an intravenous tubing 40 or patient conduit to the catheter assembly 10. In some embodiments, the flange 32 includes a set of threads 30. The threads 30 are generally provided and configured to compatibly receive a complementary set of threads 44 comprising a portion of a male luer or conduit coupler 42. The conduit coupler 42 is generally coupled to an end portion of the patient conduit 40 in a fluid-tight manner. In some embodiments, an inner portion of the conduit coupler 42 is extended outwardly to provide a probe member 46.

Figure 5:
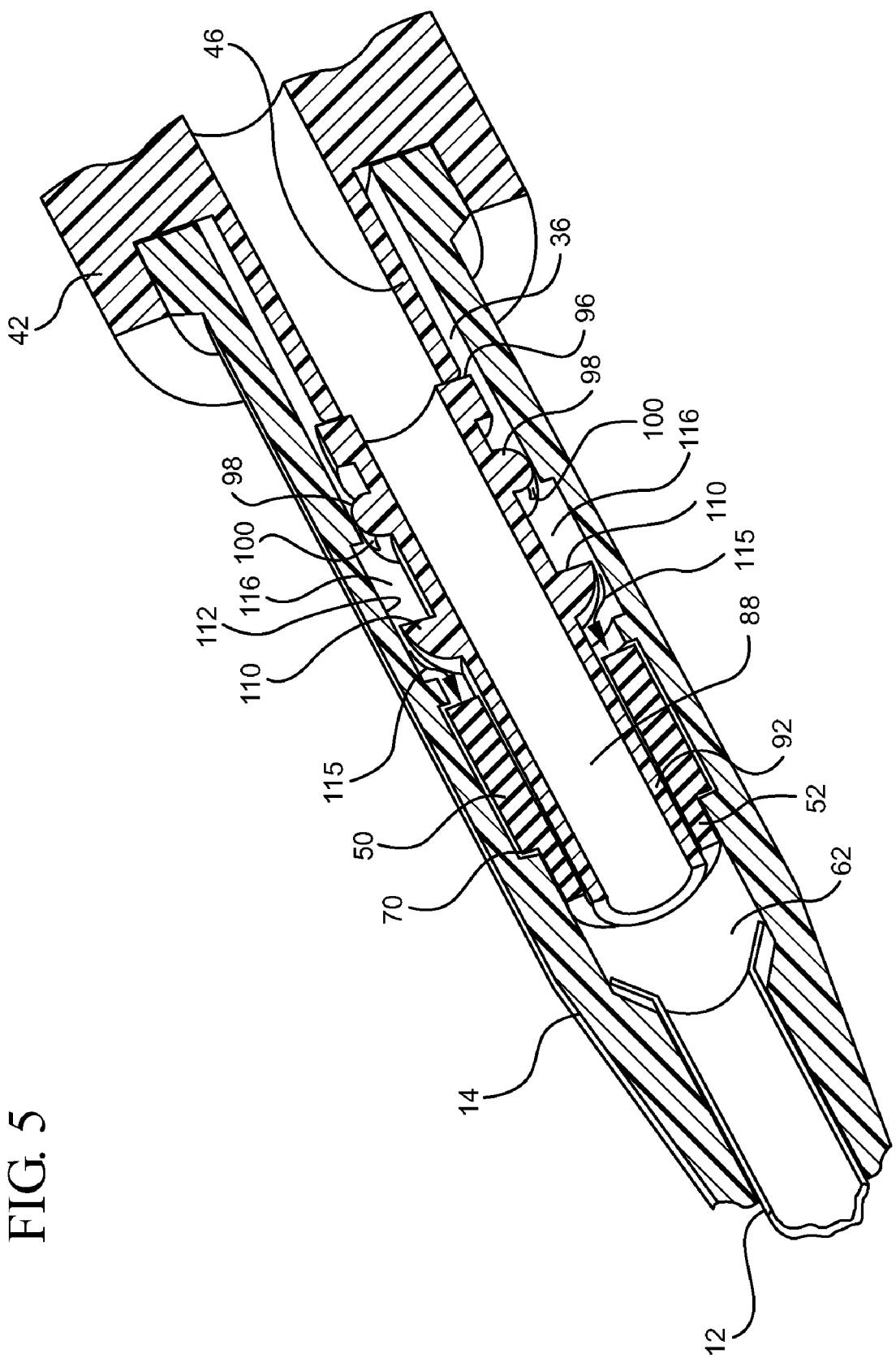
FIG. 5 is a perspective cross-sectioned view of the catheter assembly of FIG. 4 after septum activation, according to some embodiments.
Figure 6:
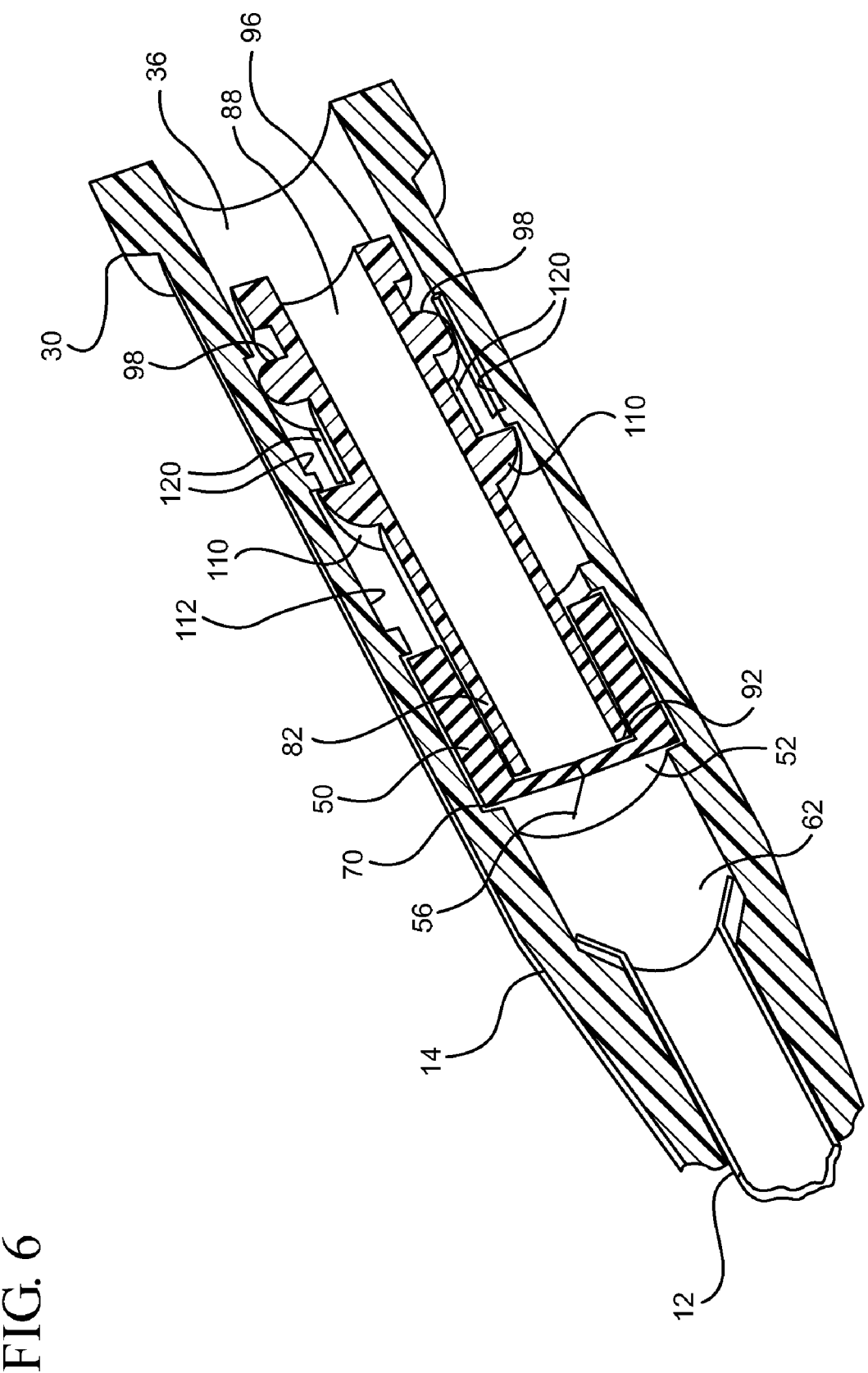
FIG. 6 is a perspective cross-sectioned view of another catheter assembly prior to septum activation, according to some embodiments.

The probe member 46 can be compatibly inserted within a proximal end 18 of the catheter adapter 14 to activate the septum therein, thus opening a fluid path within the catheter adapter 14. In some configurations, following insertion of the probe member 46 into the proximal end 22 of the catheter adapter 14, the conduit coupler 42 is interlock with the coupler 42 and the flange 28 (via the sets of threads 30 and 44), such as by rotation. During the process of interlocking the coupler 42 and the flange 28, the probe member 46 is advanced into the lumen 36 of the catheter adapter 14 to an inserted position (as shown in FIG. 6). As shown in FIG. 5, the intravenous tubing 40 is connected to the catheter adapter 14, the probe member 46 advances into the lumen 36 of the catheter adapter 14, forcing a septum activator 80 therein to pierce through the septum 50. Piercing the septum 50 opens the septum and provides a fluid path through which fluids from the intravenous tubing 40 to flow through the pierced septum 50 and the catheter 12 into the patient. The process of piercing the septum 50 is described in detail below. As will be understood, prior to the insertion of the probing member 46, the inner lumen 36 of the catheter adapter 14 is sealed to avoid blood exposure through from flashback.

Figure 3:
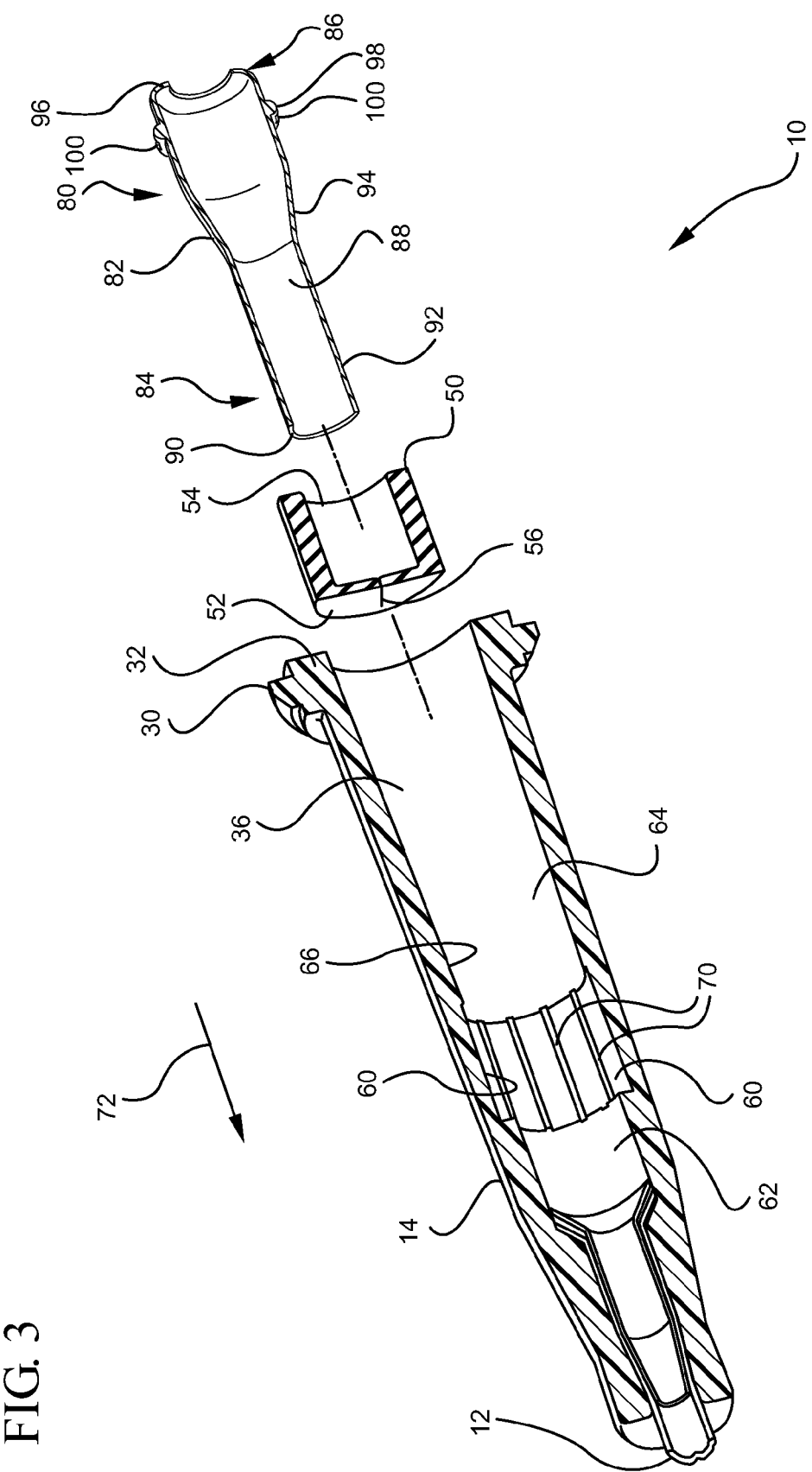
FIG. 3 is an exploded cross-sectioned view of a catheter assembly, according to some embodiments.
Figure 4:
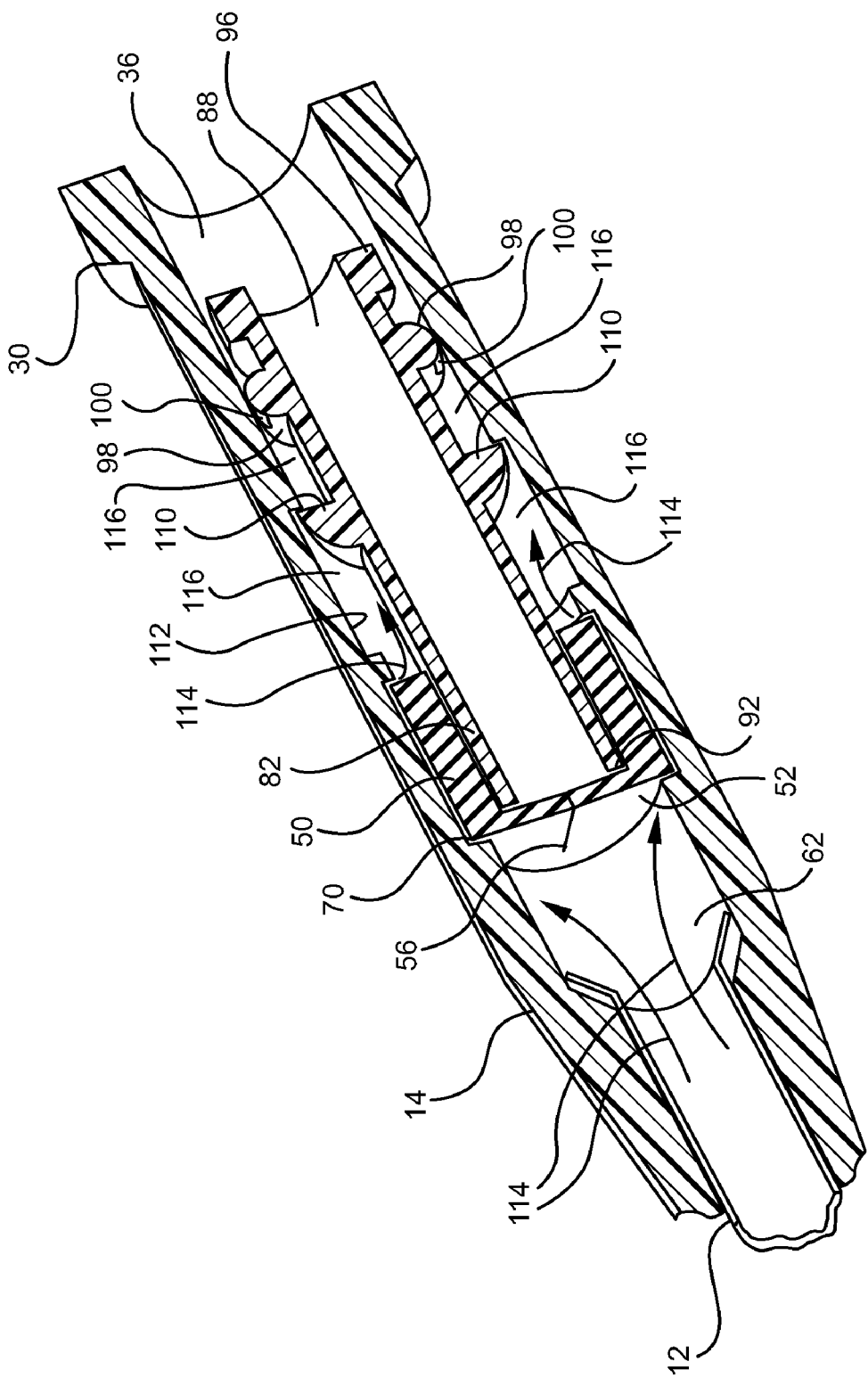
FIG. 4 is a perspective cross-sectioned view of another catheter assembly prior to septum activation, according to some embodiments.

Reference will now be made to FIGS. 3 and 4. FIG. 3 depicts an exploded, cross-sectional view of a catheter assembly 10. FIG. 4 depicts a cross-sectional view of an assembled catheter assembly 10. The septum activator 80 of FIG. 4 has an alternative structure to that of FIG. 3, as is explained below.

These figures, along with FIG. 6, depict embodiments of pierced septum valves, which include a septum having a slit that is opened and closed by the advancement and retraction of a probe-like septum activator therethrough.

As shown, in some embodiments, a septum 50 is positioned within the inner lumen 36 of the catheter adapter 14 to control the flow of fluid therein. The septum 50 generally comprises a flexible or semi-flexible polymer plug having an outer diameter that is configured to compatibly sit within a groove or channel 60 formed on an inner surface 66 of the catheter adapter 14. In some embodiments, the septum 50 is barrel-shaped and has a barrier member 52 on its distal end and a cavity 54 within its a proximal end. When positioned within the channel 60, the barrier member 52 of the septum 50 divides the inner lumen 36 of the catheter adapter 14 into a forward fluid chamber 62 and a rearward fluid chamber 64. Thus, the presence of the septum 50 can limit passage of fluid between the forward and rearward fluid chambers 62 and 64.

In some embodiments, the barrier member 52 of the septum 50 includes a slit 56. The slit 56 can provide selective access or flow of a fluid through the barrier surface 52 as it opens (activates) and closed (deactivates) in response to the septum activator 80. In some embodiments, the slit 56 is configured to remain in a closed, fluid-tight position until activated or opened by advancing a septum activator 80 through the slit 56 in a distal direction 72. In some instances, the barrier member 52 comprises a single slit 56. In other instances, the barrier member 52 is modified to include multiple slits 56, such as two slits 56 forming a cross or x-shape. In other instances, the barrier member 52 is modified to include three slits 56 forming a Y-shape.

The septum activator 80 comprises a probe-like structure serves to activate and deactivate the septum 50 in response to the insertion and removal of the probe member 46. The Septum activator 80 can be primarily housed in the rearward chamber 64 of the catheter adapter 14, proximal the septum 50. In some embodiments, the septum activator 80 is a tubular body 82 having a distal end 84 and a proximal end 86. The tubular body 82 can be made of a rigid or semi-rigid material, such as a plastic or metallic material. The tubular body 82 can have an inner lumen 88 that facilitate flow of a fluid and/or liquid through the septum activator 80 when the septum activator 80 pierces through the slit 56 of the septum 50.

The distal end 84 of the tubular body 82 can be configured to be compatibly inserted into the cavity 54 within the proximal side of the septum 50 so that it is positioned where it can pierce through the slit 56 of the barrier member 52 to form a fluid path therethrough. The distal end 84 further includes a leading surface 90 that can be inserted through the opening 54 of the septum 50 to a position proximal to the barrier member 52 of the septum 50, as shown in FIG. 6. When forced distally, the leading surface 90 advances through the slit 56 as the septum activator 80 is moved between a deactivated position, as shown in FIG. 4, to an activated position, as shown in FIG. 5.

To properly align the septum activator 80 within the inner lumen 36 of the catheter adapter 14, one or more alignment structures can be included between the outer surface of the septum activator 80 and the inner surface 66 of the catheter adapter 14. For example, as shown in FIG. 4, one or more alignment fins 110 can protrude from the outer surface of the septum activator 80 and inserted within one or more alignment groove 112 formed within the inner surface 66 of the catheter adapter 14. As the septum activator translates longitudinally within the catheter adapter, the one or more alignment fins 110 each track within the one or more alignment groove 112 to maintain septum activator 80 properly aligned within the catheter adapter 14. In some configurations there are three, four, five, or six alignment fins 110, each inserted within one of a like number of alignment grooves 112.

In addition to activating the septum 50, the septum activator 80 can form part of a flashback chamber 116 that provides an extended flashback indication to clinicians. Flashback generally occurs when the introducer needle 22 and/or the catheter 12 enter a blood vessel of a patient, piercing the blood vessel, and opening a fluid path through the catheter 12. The patient's blood pressure forces blood out the blood vessel into the catheter assembly 10. When the catheter adapter 14 or a portion thereof is transparent or semi-transparent, as it is in some embodiments, blood flow through its inner lumen 36 is observable and can indicate to a clinician that the catheter 12 is currently located within the blood vessel of the patient. If blood flow stops, the clinician can understand that the catheter 12 is no longer located within the blood vessel or that some other factor is restricting blood flow through the catheter 12. Thus, a flashback that can last long enough for a clinician to properly place a catheter is desirable.

Referring to FIG. 4, in some embodiments, the blood generally enters the catheter assembly 10 and follows a flashback path 114 through the catheter assembly 10. The fluid path 114 enters into the forward chamber 62, which can be a first flashback chamber since it includes the volume that can be observed to be filled with blood. Next, blood flows through flow restrictors 70 disposed around the septum 50 and enters the flashback chamber 116, which can be a second flashback chamber. In instances where the catheter adapter 14 or a portion thereof is transparent or semi-transparent, a clinician can observe this flow of blood filing these chambers, which indicates proper placement of the catheter 12.

As mentioned, during flashback, blood enters the flashback chamber 116 through one or more flow restrictors 70 interposed between the septum 50 and the inner surface 66 of the catheter adapter 14 to provide a flow path for flashback. Generally, the septum 50 sits within a groove or channel 60 that comprises a recessed portion of the inner surface 66 of the catheter adapter 14. The outer diameter of the septum 50 can compatibly and securely sit within the channel 60. For example, in some embodiments the outer diameter of the septum 50 is selected to be both slightly smaller than the diameter of the channel 60 and slightly larger than the diameter of the inner lumen 16. As such, the septum 50 is retained within the channel 60 during use of the catheter assembly 10. The flow restrictor 70 can permit the passage of air and fluid therethrough, while generally regulating the flow rates. The size of the cross-sectional area of each flow restrictor can at least partially control the rate of fluid flowing therethrough. For example, as the cross-sectional area of the flow restrictors 70 increases, the potential rate of fluid flow through the flow restrictors 70 increases. Likewise, flow restrictors 70 having smaller cross sectional areas will decrease the flow of fluid therethrough. The sizes and configurations of flow restrictors 70 and other components are described in detail below.

The septum activator 80 in combination with the catheter adapter 14 and the septum 50 define the flashback chamber 116, shown in FIG. 4. In some configurations, the outer surface 92 of the septum activator 80 provides a fluid barrier that prevents fluid from flowing between the inner lumen 88 of the septum activator 80 and the volume of space around the outer surface 92 of the septum activator 80. Accordingly, as shown, in some instances, the septum activator 80 is a solid tube having only two openings: a proximal and a distal opening.

Figure 8:
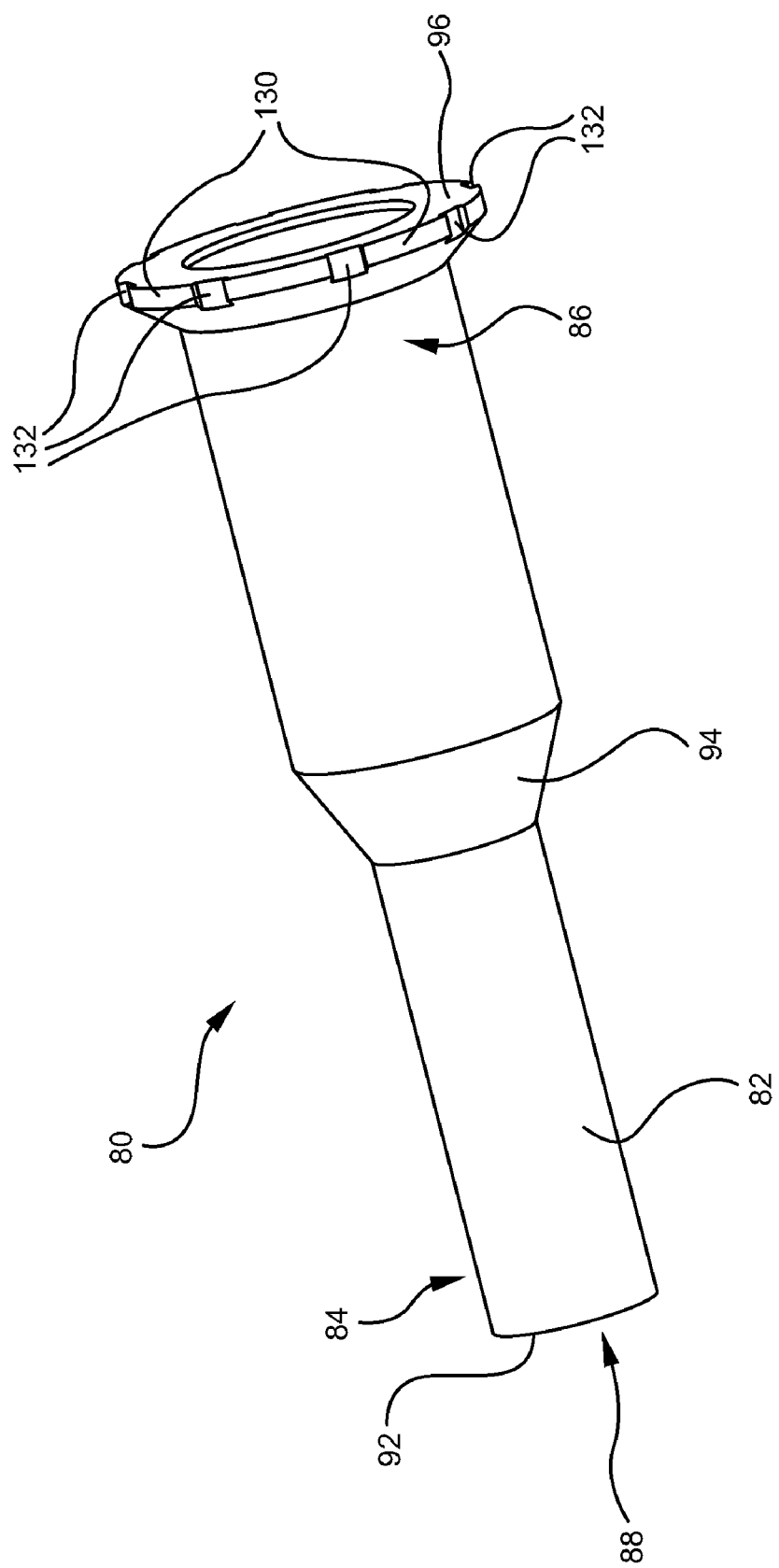
FIG. 8 is a perspective view of another septum activator, according to some embodiments.

As fluid enters the flashback chamber 116, a seal 98 disposed between the septum 50 and the inner surface 66 of the catheter adapter 14 can prevent the fluid from flowing out the proximal end of the catheter adapter 14. In some embodiments, the seal 98 encircles the septum activator 80, as shown. In some embodiments, the seal 98 is coupled to the outer surface 92 of the septum activator 80 to prevent the proximal flow of fluids past the seal 98. In other embodiments, the seal 98 can be coupled to the inner surface 66 of the catheter adapter 14. By adjusting the location of the seal 98, the volume of the flashback chamber 116 increases or decreases. Thus, the seal 98 can be positioned at various locations between the proximal and distal ends of the septum activator 80. For instance, the seal 98 can be disposed on a proximal portion of the septum activator 80, such as the proximal half of the septum activator 80, as shown. More specifically, in a non-limiting example, the seal 98 is disposed on the proximal end 86 of the septum activator 80, as shown in FIG. 8, which is described below. Further, the seal 98 can circumscribe a portion of the outer surface 92 of the septum activator 80 in a ring-like fashion, as shown, to seal the area around a portion of the septum activator 80.

In some embodiments, the seal 98 can provide a fluid-tight barrier about the septum activator 80 that prevents blood from leaking through the proximal end of the flashback chamber 116 and out the catheter assembly 10. For instance, the seal 98 can have an outer diameter greater than or equal to the inner diameter of the lumen 36 of the catheter adapter 14 to block fluid flow through the entire area between the septum activator 80 and the catheter adapter 14. The seal 98 can also be made of a flexible material so that it can adequately conform to the inner surface 66 of the catheter adapter 13 to form a seal thereon. Accordingly, the seal 98 can comprise a non-rigid material, such as an elastomeric material. In other instances, the seal 98 is made of other flexible, semi-flexible, or semi-rigid materials that can provide a fluid-tight seal between the catheter adapter 14 and the septum activator 80.

Initially during flashback, blood flowing into the catheter 12 forces air to flow through the flow restrictors 70. This initial infusion of blood can be very quick as blood rushes through the catheter 12 into the forward chamber 62. The forward chamber 62 can serve as a first flashback chamber that provides a first indication to clinicians that blood is flowing into the catheter assembly 10. By observing this flow of blood, a clinician can verify that the catheter 12 has entered a blood vessel. However, in some instances, the time in which this initial flashback occurs is very quick and not long enough for a clinician to verify proper catheter placement. Accordingly, in some configurations, a second flashback chamber 116 is provided on the proximal side of the septum 50 that provides extended flashback indications. Accordingly, air and blood from within the forward chamber 62 can flow through the flow restrictors 70 disposed between the septum 50 and the catheter adapter 14 into the second flash chamber 116. Because the size of the flow restrictors 70 controls the flow of blood therethrough, the rate of flashback into the second flashback chamber 116 can be regulated to provide a longer average flashback periods.

When blood begins to flow into the catheter assembly, a positive pressure develops within the forward chamber 62, the first flashback chamber, and the second flashback chamber 116. This pressure can reduce or prevent the flow of blood into the catheter assembly 10, thus preventing a desired flashback of the patient's blood into the catheter adapter 14. Thus, some embodiments include features or elements to enable airflow through or around the seal 98, to relieve this positive pressure by permitting air, but not blood, to exit therethrough. As such, some embodiments of the present invention provide a complete observable flashback, as generally desired for infusion procedures.

Figure 7:
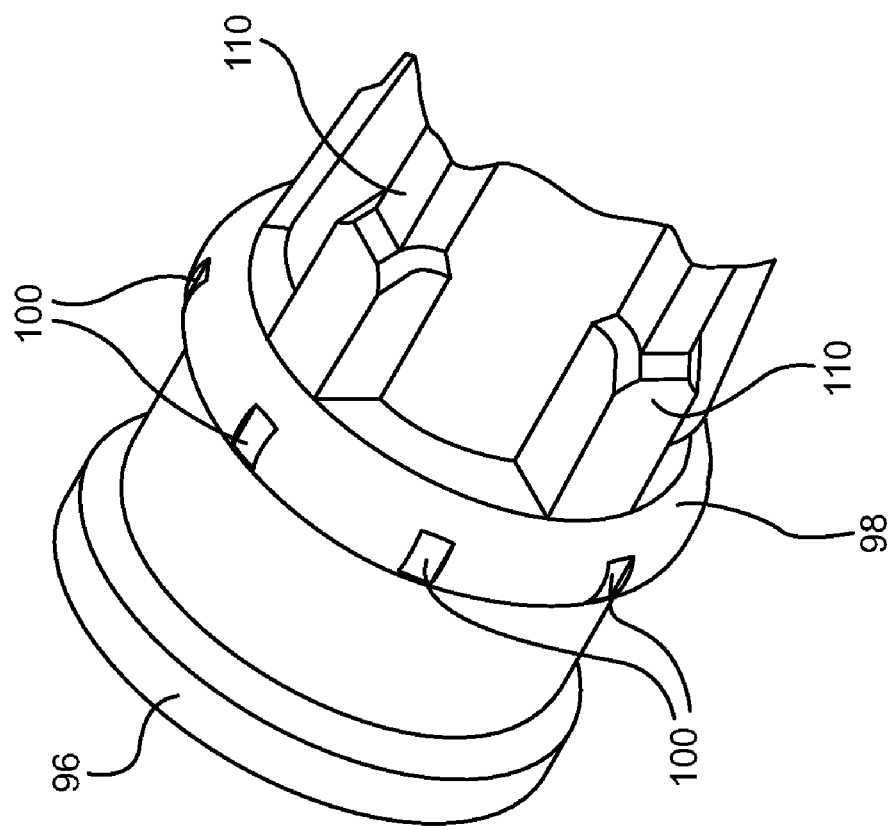
FIG. 7 is a partial perspective view of a seal on a septum activator, according to some embodiments.

In some embodiments, the seal 98 of the septum activator 98 is modified to include one or more vents 100. In other embodiments, one or more vents 120 (shown in FIG. 6), in the form of channels, are interposed between the seal 98 and the inner surface 66 of the catheter adapter 14. These vents 100 relieve the positive pressure within the flashback chambers 62, 116 by providing an access for air to bypass the seal 98 into the exterior environment. In some embodiments, the vents 100 are constructed by removing portions of the seal 98 surface, resulting in a plurality of generally parallel grooves. A close-up perspective view of a seal 98 having multiple vents 100 is depicted in FIG. 7. In other embodiments, the vents 100 are formed as channels through the seal 98 rather than on the surface of the seal 98.

In some embodiments, the rate at which air and/or fluid flows through the vents 100 in the seal 98 is adjusted by manufacturing the catheter adapter 14 to include a greater or lesser number of vents 100 or by changing the cross-sectioned area of the vents 100. Thus, in some embodiments the rate at which air and/or fluid flows out of the second flashback channel 116 is increased by manufacturing a catheter adapter 14 to have either an increased number of vent 100, or vents 100 with a greater cross-sectioned area. Conversely, in other embodiments the rate at which air and/or fluid flows from the second flashback chamber 116 is decreased by manufacturing a catheter adapter 14 with either a decreased number of vents 100, or vents 100 having a lesser cross-sectioned area.

One having skill in the art will appreciate that the blood pressure of the patient is largely responsible for the rate at which blood and air flow through the septum 50 and the vents 100 in or around the seal 98. As such, the flow rate through the system is affected by the combined effective hydraulic diameter of all flow paths. Thus, in some embodiments, the hydraulic diameter of the vents 100 is modified to increase or decrease the rate of flow through the catheter assembly 10. In other embodiments, the hydraulic diameter of the vents 100 are decreased thereby resulting in substantially reduced or stopped flow through the ventilation means. The governing equation for controlling the flow rate through the ventilation means is given in Equation 1, where BP is the blood pressure, A is the surface area of the ventilation means, ó is the surface tension of the blood, and P is the perimeter of the ventilation means.

$$BP(A)=\sigma(P) \qquad \text{Equation 1:}$$

Thus, according to Equation 1, when the perimeter of a vent is small, the vents 100 will allow air venting, but will prevent blood flow due to the relatively high surface tension ($\sigma$) of blood. However, when the perimeter of the vent is increased, the surface tension between the blood and the vent 100 is decreased thereby enabling the blood to slowly leak through the vents and around the septum to provide desirable, yet controlled flashback. Therefore, by adjusting the variable of Equation 1, a desired flow will be achieved. Thus, based on the size and/or number of vents around the septum, the catheter assembly design will provide customized, controlled, and predictable blood flow through the seal 100.

In some embodiments, the one or more vents 100 are designed to allow the flow of air and stop the flow of blood. In some embodiments, the number of vents 100 is between 1 and 40. In other embodiments, the number of vents 100 is between 1 and 20. In some embodiments, six or more vents 100 are included. While in other embodiments, five or fewer vents 100 are included. Accordingly, in some embodiments, the vents 100 have a cross sectional area between about 0.000007 to 0.00004 inches$^2$. In other embodiments, the vents 100 have a cross sectional area between about 0.00001 to 0.00003 inches². In other embodiments, the vents 100 have a cross sectional area of about 0.00002 inches². For instance, in some embodiments, the vents 100 have a height of about 0.001 to 0.003 inches and a width of about 0.010 inches. In other embodiments, the vents have a height of about 0.002 to 0.003 inches and a width of about 0.005 inches.

Similarly, the one or more flow restrictors 70 between the septum 50 and the inner surface 66 of the catheter adapter 14 can be specifically configured to permit blood and air to pass therethrough at an estimated range of flow rates. For instance, the one or more flow restrictors 70 can permit blood to flow therethrough at a rate between about 10 to 200 ml/hr. In other instances, the one or more flow restrictors 70 can permit blood to flow therethrough at a rate between about 15 to 150 ml/hr. In yet other instances, the one or more flow restrictors 70 can permit blood to flow therethrough at a rate between about 50 to 100 ml/hr. At these rates, the rate of blood flow into the flashback chamber 116 can be paced to provide a clinician with adequate time to correctly locate the catheter within a patient's blood vessel. Accordingly, in some embodiments, the flow restrictors 70 have a cross sectional area greater than 0.00003 inches². In other embodiments, the flow restrictors 70 have a cross sectional area greater than 0.00004 inches². In other embodiments, the vents 100 have a cross sectional area of about 0.0001 inches². In other embodiments, the vents 100 have a cross sectional area of about 0.001 inches².

Referring now to FIG. 5 a cross-sectional view of the catheter assembly 10 is shown following activation of the septum 50 via the septum activator 80. Upon insertion of the coupler 42 into the proximal opening 26 of the catheter adapter 14, the probe member 46 of the coupler 42 contacts the contact surface 96 of the septum activator 80. The septum activator 80 is advanced in a distal direction 72 as the coupler 42 is further inserted into the lumen 36 of the catheter adapter 14. As the coupler 42 is advanced farther into the lumen 36, the probing surface 92 of the septum activator 80 passes through the barrier member 52 of septum 50. As such, the probing surface 92 of the septum activator 80 is positioned within the forward chamber 62 providing a fluid pathway through the opened slit 56 of the septum 50.

During septum activation, the volume of the flashback chamber 116 decreases as the septum activator 80 advances in the distal direction 72. The decrease in volume can create a positive pressure within the flashback chamber 116 that can cause fluids within the flashback chamber 116 to flow back through the flow restrictors 70 into the forward chamber 62, along the fluid flow path 115. This fluid can then be flushed out the catheter assembly 10 with the infusion of fluids from the intravenous tubing 40.

In some embodiments, the catheter assembly 10 is configured to permit the septum activator 80 to return to a deactivated position entirely within the rearward chamber 64 following removal of the coupler 42 from the catheter adapter 14. Thus, when the coupler 46 is removed or detached from the catheter assembly 10, the fluid pathway through the septum 50 is reclosed.

Referring will now be made to FIG. 6, which depicts a catheter assembly 10 similar to that of FIG. 4. However, as shown, in some embodiments, the seal 98 does not include vents 100. Rather, as shown in FIG. 6, one or more vents 120 are formed into the inner surface 66 of the catheter adapter 14. In some configurations, the one or more vents 120 extend along the length of the inner surface 66 of the catheter adapter 14 at least at each location where the seal 98 contacts the catheter adapter 14 as it is moved from a deactivated position to an activated position. This configuration can permit air venting through the one or more vents 120 regardless of the location of the septum activator 80. In other configurations, the one or more vents 120 extend only across the location where the seal 98 contacts the inner surface 66 of the catheter adapter 14 in a deactivate position, the position shown in FIG. 6. As mentioned, the dimensions of the vents 120 can be selected to permit the flow of air but not gas therethrough. These dimensions can be substantially similar to those referenced above for the vents 100 within the seal 98.

Referring will now be made to FIG. 8, which depicts a septum activator 80 that has an alternative seal configuration. As shown, the septum activator 80 includes a tubular body 82 with a distal end 84 and a proximal end 86. A seal 130 is disposed on the distal end 86 of the septum activator 80, which will provide the largest possible length of flashback chamber 116. Vents 132 are formed in the seal similar to those previously mentioned. In some embodiments, the seal 130 is integrated into the septum activator, such that the two form a single piece structure. In some embodiments, the septum activator 80 and the seal 130 are made of the same material. In other embodiments, the septum activator 80 and the seal 130 are made of different materials that are connected in a fluid-tight manner.

Figure 9:
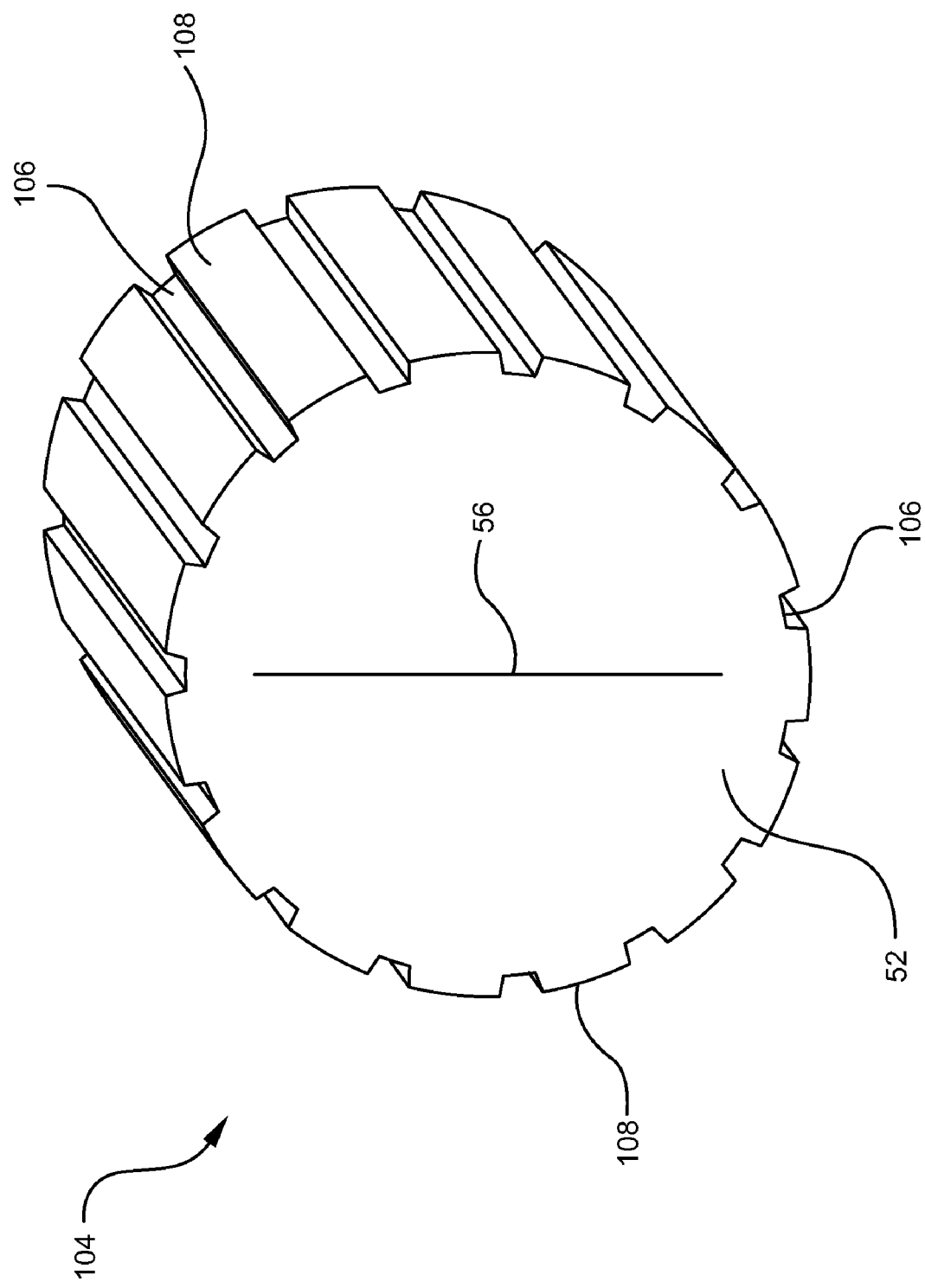
FIG. 9 is a perspective view of a septum, according to some embodiments.

Referring now to FIG. 9, an embodiment of a septum 104 is shown. In some embodiments, an outer surface 108 of the septum 104 is modified to include a plurality of recessed grooves 106. The recessed grooves 106 provide pathways between the forward and rearward chambers 62 and 64 through which air and/or fluid may flow. Thus, in some embodiments, the channel 60 does not include air flow restrictor channels 70, but rather the outer surface 108 of the septum 104 is modified to provide desired flow between the forward and rearward chambers 62 and 64. The shape and size of these grooves can be selected, as mentioned, to provide the desired flow rate therethrough. For instance, the one or more flow restrictors 132 can permit blood to flow therethrough at a rate between about 10 to 200 ml/hr. In other instance, the one or more vents 132 can permit blood to flow therethrough at a rate between about 15 to 150 ml/hr. In yet other instances, the one or more vents 132 can permit blood to flow therethrough at a rate between about 50 to 100 ml/hr.

From the foregoing, it can be seen that a pierced septum valve can provide selective activation of fluid flow through the catheter assembly while minimizing or eliminating blood exposure. Additionally, the pierced septum valve can enhance a clinician's ability to confirm catheter placement by providing an additional flash chamber between a seal around the exterior of the septum activator and the septum.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A pierced septum valve comprising:
 a septum disposed within a lumen of a body;
 a septum activator disposed proximal the septum within the lumen of the body;
 a seal disposed between an outer surface of the septum activator and the body; and
 one or more vents formed in the seal and disposed between the seal and the lumen of the body, the one or more vents each having a cross sectional area that permits the passage of air but not blood.

2. The pierced septum valve of claim 1, wherein the cross sectional area of each vent is between 0.0001 to 0.0003 inches$^2$.

3. The pierced septum valve of claim 2, wherein the one or more vents includes six or more vents.

4. The pierced septum valve of claim 3, wherein the seal encircles the septum activator.

5. The pierced septum valve of claim 1, wherein the one or more vents are formed in the exterior of the seal.

6. The pierced septum valve of claim 1, wherein the one or more vents are formed through the seal.

7. The pierced septum valve of claim 1, wherein the one or more vents are channels formed in the body.

8. The pierced septum valve of claim 1, wherein the body is a catheter adapter and the lumen of the body extends through the catheter adapter.

9. The pierced septum valve of claim 1, wherein the seal has an outer diameter greater than or equal to an inner diameter of the lumen.

10. The pierced septum valve of claim 1, wherein the seal includes an elastomeric material.

11. The pierced septum valve of claim 1, wherein the seal is disposed about a proximal portion of the septum activator.

12. A catheter assembly comprising:
   a catheter adapter having a lumen extending therethrough;
   a septum disposed within the lumen;
   one or more flow restrictors disposed between the septum and the catheter adapter;
   a septum activator disposed within the lumen proximal the septum;
   a seal disposed between an outer surface of the septum activator and the catheter adapter; and
   one or more vents formed in the seal and disposed between the seal and the lumen of the body.

13. The catheter assembly of claim 12, wherein the one or more vents disposed between the seal and the lumen of the body each have a cross sectional area between 0.0001 to 0.0003 inches$^2$.

14. The catheter assembly of claim 12, wherein the one or more flow restrictors include one or more openings each having a cross sectional area of greater than 0.0003 inches$^2$.

15. The catheter assembly of claim 12, wherein the volume exterior the septum activator between the septum and the seal forms a flashback chamber.

16. The catheter assembly of claim 12, wherein the septum activator has a substantially tubular-shaped body with a lumen extending therethrough.

17. The catheter assembly of claim 16, wherein the seal has an outer diameter greater than or equal to an inner diameter of the lumen at the locations.

18. The catheter assembly of claim 17, wherein the seal is disposed about a proximal portion of the septum activator.

19. The catheter assembly of claim 18, wherein the seal includes an elastomeric material.

20. A catheter assembly comprising:
   a catheter adapter having a lumen extending therethrough;
   a septum disposed within the lumen;
   one or more flow restrictor channels disposed between the septum and the catheter adapter, the cross sectional area of the one or more flow restrictor channels being greater than 0.0003 inches$^2$;
   a septum activator disposed within the lumen proximal the septum, the septum activator having a substantially tubular-shaped body;
   an annular seal disposed between an outer surface of the septum activator and an inner surface of the lumen, the seal being disposed about a proximal portion of the septum activator; and
   one or more vents formed in the seal and disposed between the seal and the lumen of the body, the one or more vents each having a cross sectional area between 0.0001 to 0.0003 inches$^2$ and each permit the passage of air but not blood.

* * * * *